United States Patent [19]

Mamadzhanov et al.

[11] 4,347,736
[45] Sep. 7, 1982

[54] CONTINUOUS BOREHOLE-LOGGING METHOD

[76] Inventors: Ulmas D. Mamadzhanov, kvartal Ts-1, dom 19, kv. 25; Vitold M. Bakhir, proezd Gaidara, 7a, kv. 17; Stanislav A. Alekhin, Chilan zar, kvartal 24, dom 53, kv. 89; Tatyana M. Bakhir, proezd Gaidara, 7a, kv. 17, all of Tashkent, U.S.S.R.

[21] Appl. No.: 224,551

[22] PCT Filed: Nov. 28, 1979

[86] PCT No.: PCT/SU79/00118
§ 371 Date: Nov. 27, 1980
§ 102(e) Date: Nov. 25, 1980

[87] PCT Pub. No.: WO80/02053
PCT Pub. Date: Oct. 2, 1980

[30] Foreign Application Priority Data

Mar. 26, 1979 [SU] U.S.S.R. ................................ 2736516

[51] Int. Cl.³ .............................................. E21B 49/00
[52] U.S. Cl. .............................................. 73/155; 175/40
[58] Field of Search ................. 73/155, 153; 324/438; 175/40; 23/230 EP

[56] References Cited

U.S. PATENT DOCUMENTS 3,722,606 3/1973 Fertl et al. ...................... 73/153 X
3,802,259 4/1974 Eckels .................................. 73/153

*Primary Examiner*—Jerry W. Myracle
*Attorney, Agent, or Firm*—McAulay, Fields, Fisher, Goldstein & Nissen

[57] ABSTRACT

A method of continuously logging a borehole in the course of drilling with the use of a drilling mud. According to the invention, the drilling mud fed into the borehole is subjected to unipolar electric treatment, with simultaneous measurement of the oxidation-reduction potential of the drilling mud. This value is maintained substantially constant at a given magnitude. The value of the oxidation-reduction potential of the drilling mud returning from the borehole is continuously measured and compared with the given value of the oxidation-reduction potential of the drilling mud fed into the borehole. Using the difference between the two values, the mineralogic composition of the rock adjacent to the bottom of the hole is determined for a given moment, by comparing this difference with the known in advance normal oxidation-reduction potentials of minerals.

1 Claim, 2 Drawing Figures

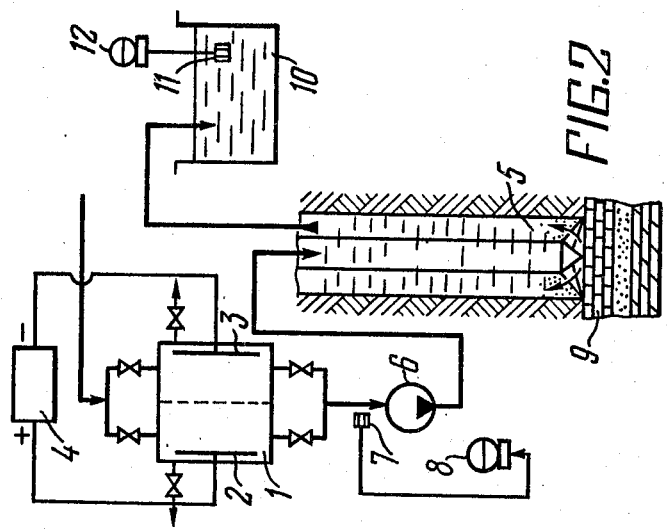
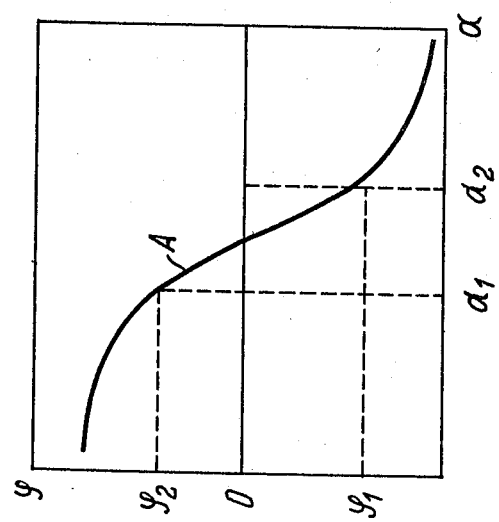
FIG.1
FIG.2

CONTINUOUS BOREHOLE-LOGGING METHOD

TECHNICAL FIELD

The invention relates to the technology of drilling boreholes or wells, and more particularly it relates to the methods of continuously logging a well or borehole being drilled.

The invention can be employed to utmost effectiveness in geological survey work when prospecting survey wells.

The invention can be also effectively used in natural fuel gas and oil production for determining the lithological properties of the rock traversed by a production well being drilled.

BACKGROUND ART

At present, the lithological composition of a rock being drilled is determined by obtaining a sample of the rock by a core bit and subsequently analysing the texture and mineralogical composition of the rock. This technique is characterized by its time- and labour-consuming character, and, hence, by its high cost.

There are also widely known methods of determining the tectonics, structure and lithology of rock with aid of electric-logging charts obtained by conducting electric logging while drilling a borehole or well. The methods are likewise characterized by their highly labour-consuming character, because in order to conduct the logging, the drilling tool has to be pulled out of the borehole, the appropriate instruments have to be run into borehole on the cable, and the data obtained has to be subsequently interpreted and analysed.

There are further known methods of determining the lithological composition of the rock in a borehole by using the drilling cuttings entrained in the upward flow of the drilling mud. The drilling cuttings are employed according to these methods for determining the texture and the mineralogical composition of the rock strata traversed by the borehole, by using laboratory methods.

However, these last-mentioned known methods are characterized by the insufficiently accurate information they yield, since it cannot be always positively known to which traversed stratum these or other drilling cuttings belong, to say nothing of the considerable time it takes to investigate the mineralogical composition of the samples of the drilling cuttings.

DISCLOSURE OF THE INVENTION

The present invention has for its aim the creating of a continuous borehole-logging method, wherein the physical parameter used should enable to determine the lithological composition of the rock strata traversed by the borehole in a rapid, accurate and relatively simple manner.

This aim is attained in a continuous borehole-logging method in the course of drilling with the use of a drilling mud, which method, in accordance with the invention, includes subjecting the drilling mud fed into the borehole to unipolar electric treatment, while measuring its oxidation-reduction potential and maintaining this value substantially permanent at a given magnitude; continuously measuring the value of the oxidation-reduction potential of the drilling mud returning from the borehole and comparing this value with the given value of the oxidation-reduction potential of the drilling mud fed into the borehole, and using the difference between the two values at any given moment to determine the mineralogical composition of the rock adjacent to the bottom of the borehole by comparing said difference with the known in advance normal oxidation-reduction potentials of minerals.

The proposed method enables to enhance the accuracy of the determination of the lithological composition of the rock, owing to the direct contact of the rock with the drilling mud being accompanied by processes of ion exchange therebetween, such processes altering the major parameters of the drilling mud, and of its oxidation-reduction or redox potential, in particular.

Furthermore, the proposed method enables to simplify and speed up the determination of the lithological composition of the rock, eliminating as it does such labor-consuming operations as taking core samples or sampling the drilling cuttings, as well as the operations involved in electric logging of boreholes.

BRIEF DESCRIPTION OF THE DRAWINGS

The invention will be further described in connection with an embodiment thereof, with reference being made to the accompanying drawings, wherein:

FIG. 1 shows a curve illustrating the relationship between the respective activities "$a_{ox}$" of the oxidized form of a matter and "$a_{red}$" of the reduced form thereof;

FIG. 2 illustrates schematically the pattern of circulating the drilling mud for performing the disclosed method.

BEST MODE FOR CARRYING OUT THE INVENTION

Those competent in the art know that a drilling mud in its general form is a heterogeneous fluid system always containing the particles of solid phase, low-molecular ions and polyelectrolytes—polymers of which the molecules contain groups capable of ionization in a solution. The presence in the drilling mud of these components is a prerequisite of ensuring the most essential properties of the drilling muds from the well-drilling point of view. Among these properties, in the first place, is the capability of the mud to exhibit the minimized physical and chemical action on the rock making up the borehole walls, to create the minimized disturbance of the thermodynamic, chemical and physical processes taking place at the borehole-formation interface. This major condition requires maintaining the stability of the drilling mud, i.e. maintaining stable its major characteristics throughout the drilling time, notwithstanding the action of aggressive salts, i.e. the salt resistance of the mud.

The polyelectrolytes, i.e. the chemical agents employed for stabilization of the properties of drilling muds provide protection to the particles and phases of the dispersion system which is the drilling mud against the adverse action of the environment to which the dispersion system is exposed in the course of the drilling.

Furthermore, they are absorbed on the surfaces of the solid phase particles, modifying this surface, forming a solvate shell, and thus enabling to consider the properties of the surface of the solids as that of a single two-dimensional macromolecule of a polyelectrolyte.

On the other hand, the lyophilic portions of the solid phase particles, which have not absorbed polyelectrolyte molecules, are altogether similar to the latter by their physical and chemical properties. Like true molecules of higher polymers, they have groups capable of ionization in a solution (the silanol groups), and they also are capable of retaining at their surface low-molecular ions and hydration water molecules.

Therefore, one of the essential conditions of determining the stability of drilling muds is the evaluation of the physical and chemical equilibrium of the polyelectrolytes in the drilling mud concerned.

The size of the molecules of the polyelectrolytes, same as their other properties, may vary within a range far broader than that associated with common macromolecules. The polyelectrolytes can be classified or divided into polyacids, polybases and polyampholytes or polyamphibolytes (i.e. copolymers containing both basic and acidic groups).

Among the chemicals or chemical agents employed for treating drilling muds there are the representatives of all the abovelisted classes or groups. The majority of the polyelectrolytes include weak acidic or basic groups (e.g. carboxy groups such as carboxymethyl cellulose, or amino groups). Therefore, they can be ionized only in the presence of a strong alkali (in case of polyacids), or of a strong acid (in case of polybases). In this case the chain of the polyelectrolyte has bound thereto charged groups, while the surrounding medium contains low-molecular ions of the opposite sign, i.e. the counterions.

The properties of molecules of polyelectrolytes in a solution are defined by the presence of electrostatic interaction of the electrically charged groups of a chain with one another and with the low-molecular ions of the solution which latter, as a whole, is usually electrically neutral.

Experimentally obtained data (particularly those obtained from experiments with transfer of labelled or traced Na and from measuring the activity coefficients of low-molecular ions) have proved that the molecule of a polyacid or polybase usually attracts and retains adjacent thereto a considerable number of solvated (or hydrated) counter-ions, this number more often than not being more than one half of the number of the charged groups of the chain.

The electrostatic repelling of the similarly charged groups in polyacids and polybases results in a sharp alteration of the conformity properties of the macromolecules, particularly, in the swelling of their size in a solution, which is usually a major asset from the point of view of the quality of drilling muds.

The mean size of the molecules of polyelectrolytes are able, with an increased degree of ionization, to swell fivefold or even more. The increased concentration of lowmolecular ions in a solution, i.e. the ion strength of the solution affects the interaction of the charged groups and brings the sizes and other properties of the molecules of polyelectrolytes closer to those of common macromolecules, whereby the acticity of the molecules of the polyelectrolytes significantly decreases.

It can be seen from the abovesaid that the variation of the concentration of low-molecular ions in a solution (i.e. of inorganic acids, acids and bases) displays the same mechanism of affecting the polymer electrolytes and the lyophilic portions of the solid phase particles, which is exhibited in the variation of the intensity and character of interaction of the charged groups of macromolecules with the surrounding medium. This variation is closely associated with the oxidation-reduction equilibrium of the molecules of a polyelectrolyte in a solution, determining as it does the possibility of electron exchange between the macromolecule and the low-molecular ions, atoms and molecules surrounding it and constituting the dispersion medium of the drilling mud. Thus, the ratio of the oxidized and reduced forms of the matter in the drilling mud plays a decisive role as far as the stability of the polyelectrolyte molecules, and, hence, of the drilling mud as a whole, and its salt resistance are concerned.

Quite naturally, every reaction altering the activity of organic substances in the drilling muds results in the varying degree or state of the oxidation of the macromolecules of polyelectrolytes, which is the case, for instance, with thermal-oxidation destruction of carboxymethyl cellulose.

Oxidation-reduction reactions are those involving mutual oxidation or reduction of various substances.

Oxidation of a substance involves removal of electrons from its components, while reduction involves addition of electrons. When an electrode made of an inert metal is immersed in a liquid, there is created at the electrode-solution interface a voltage difference which is the oxidation-reduction potential, also referred to in the present disclosure as the redox potential.

The value of the redox potential of a system is a measure of the intensity of oxidation-reduction processes taking place in the system, depending on the ratio therein of the concentrations of the oxidized and reduced forms of the ions either making up the system or introduced thereinto.

Therefore, to evaluate the stability of drilling muds, it is possible to resort to the measurement of the oxidation-reduction potential of the system, which is representative of the ratio of the oxidized and reduced components in the drilling mud.

The redox potential "$\phi$" of a solution with the oxidizing activity "$a_{ox}$" and reducing activity "$a_{red}$" is determined by the Nernst equation:

$$\rho = \rho_o + \frac{RT}{ZF} \ln \frac{a_{ox}}{a_{red}},$$

where
- $\phi_o$ is the normal potential of an inert (platinum or gold) electrode, mV;
- R is the universal gas constant;
- T is the temperature, °K;
- z is the number of the electrodes taking part in the reaction;
- F is the Faraday constant, and
- ln is the symbol of natural logarithm.

This formula enables to plot the curve (curve "A" in FIG. 1) of the relationship between the redox potential "$\phi$" and the ratio of the activites "$a_{ox}$" and "$a_{red}$", respectively, of the oxidized and reduced forms of the matter, which has the general shape illustrated in FIG. 1.

Under stationary conditions, i.e. those characterized by very slow variation with time of the conditions of energy exchange with the neutral environment, the redox potential of a drilling mud usually acquires the equilibrium value corresponding to the ratio $a_{ox}:a_{red}=0.5:1$. Such an important indicator of the chemical activity of the system as the pH number acquires under these conditions the neutral value of pH=7.

Any variation of these two variables from the positive equilibrium means that the system becomes unstable energy-wise and is capable of oxidation-reduction reactions with the environment, e.g. the rock of the borehole walls, as well as within the system itself, i.e. between its particles and phases.

Depending on its lithological properties, the rock making up the walls of a borehole may contain a great number of various minerals which, when contacted by an electrolyte, i.e. the drilling mud, alter the redox potential of the mud, such alteration being possible within a significantly broad range.

Given as an illustration in Table 1 hereinbelow are the normal oxidation-reduction potentials $\epsilon_o$ corresponding to eventual electrochemical reactions of interaction of various ions contained in the crystal lattice of rock-forming minerals with a liquid, e.g. water or drilling mud.

TABLE 1

| Reactions | $\epsilon_o$V |
|---|---|
| $Cr^{3+} + e^-$ | $-0.41$ |
| $Sn^{4+} + 2e^-$ | $+0.153$ |
| $Cu^{2+} + e^-$ | $+0.167$ |
| $Fe^{3+} + e^-$ | $+0.771$ |
| $Mn^{3+} + e^-$ | $+1.51$ |

As it can be seen from the Table, different minerals display significantly different normal redox potentials. Therefore, when in the course of drilling a borehole or well the drilling mud which initially has had the equilibrium state contacts the rock of the hole bottom, and we know in advance the values of the normal redox potentials of all the kinds of rock making up the formations of a given field, the change in the value and the sign of the redox potential of the mud returning from the borehole following its contact with the rock can be used to determine the lithological composition of the formation being drilled.

Let us consider a concrete example.

To determine the lithological composition of the rock traversed by a borehole, there is prepared an initial drilling mud, whereafter it is subjected to unipolar electric treatment, while measuring at the same time in the electrolized 1 (FIG. 2) the value of its redox potential.

By varying the voltage at the electrodes 2 and 3 and the current, the value of the redox potential is brought to the magnitude corresponding to the oxidation-reduction equilibrium (in case of drilling muds this magnitude is within the range of 1.6 V to +1.8 V).

In practical cases, when drilling muds are prepared, depending on the type of the clay used and on the type and ratio of the chemical agents introduced into the mud, there may prevail therein either the oxidation potential or the reduction one. To stabilize it, the mud is to be treated either in the zone of the negative electrode 2 (in this case the chemical reactions in the mud would have the reduction character), or in the zone of the positive electrode 3 (then the chemical reactions would have the oxidation character). The electrodes are supplied from a direct-current source 4.

With the drilling mud thus treated, the value of the redox potential is maintained permanent at the magnitude predetermined by the adopted technology.

The stabilized drilling mud is pumped into the borehole 5 by a pump 6. The stabilized redox potential of the treated mud is monitored by the sensor 7 responsive to the redox potential, e.g. a Kryukov's calomel-electrode sensor connected to a secondary instrument or indicator 8.

When the rock 9 is drilled, there take place in the zone of the contact of the drilling mud with the rock oxidation-reduction reactions due to the ion exchange between the drilling mud and the minerals making up the rock.

The drilling mud returning from the borehole 5 is directed into a vessel 10 where a sensor 11 and a registering device 12 connected thereto are operated to measure continuously the redox potential of the drilling mud after the latter's contact with the rock being drilled. Then the value of the redox potential of the mud returning from the borehole is compared with the preset value of the redox potential of the mud fed into the well.

By comparing the known in advance normal redox potentials of the minerals making up the formations with the value of the alteration of the redox potential of the mud returning from the well, it is relatively easy to determine the mineralogical and lithological composition of the rock being drilled at a given moment.

Industrial Applicability

The employment of the disclosed method enables to considerably cut the time required for determining the lithological composition of various types of rock with sufficient accuracy, and also to save money, energy and men-hours.

The disclosed continuous borehole logging method can yield the maximum effect in the natural fuel gas and oil production industry, when prospecting and production wells are drilled.

What is claimed is:

1. A method of continuously logging a borehole in the course of drilling with the use of a drilling mud, characterized in that it includes subjecting the drilling mud fed into the borehole to unipolar electric treatment, while measuring at the same time the value of the oxidation-reduction potential of the drilling mud, and maintaining this value substantially constant at a given magnitude; continuously measuring the value of the oxidation-reduction potential of the drilling mud returning from the borehole, comparing the last-mentioned value with the given value of the oxidation-reduction potential of the drilling mud fed into the borehole, and using the difference between the two values for determining for a given moment the mineralogic composition of the rock adjacent to the bottom of the hole, by comparing this difference with the known in advance normal oxidation-reduction potentials of minerals.

* * * * *